United States Patent
Itsuji

(10) Patent No.: US 9,012,833 B2
(45) Date of Patent: Apr. 21, 2015

(54) TERAHERTZ WAVE MEASURING APPARATUS AND MEASUREMENT METHOD

(75) Inventor: Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 77 days.

(21) Appl. No.: 13/582,833

(22) PCT Filed: Mar. 9, 2011

(86) PCT No.: PCT/JP2011/001384
§ 371 (c)(1),
(2), (4) Date: Sep. 5, 2012

(87) PCT Pub. No.: WO2011/111385
PCT Pub. Date: Sep. 15, 2011

(65) Prior Publication Data
US 2012/0318967 A1 Dec. 20, 2012

(30) Foreign Application Priority Data
Mar. 12, 2010 (JP) .................. 2010-056197

(51) Int. Cl.
*G01D 18/00* (2006.01)
*G01J 3/42* (2006.01)
*G01J 3/28* (2006.01)
(Continued)

(52) U.S. Cl.
CPC .. *G01J 3/42* (2013.01); *G01J 3/027* (2013.01); *G01J 3/28* (2013.01); *G01N 21/274* (2013.01); *G01N 21/3586* (2013.01)

(58) Field of Classification Search
USPC .................................................. 250/252.1
See application file for complete search history.

(56) References Cited

U.S. PATENT DOCUMENTS

| 7,663,107 B2 | 2/2010 | Taday |
| 2009/0198466 A1 | 8/2009 | Kajiki |
| 2009/0302223 A1 | 12/2009 | Tamada |

FOREIGN PATENT DOCUMENTS

| CN | 200996980 Y | 12/2007 |
| CN | 101126701 A | 2/2008 |

(Continued)

OTHER PUBLICATIONS

Martin van Exter et al., "Terahertz time-domain spectroscopy of water vapor," Optics Letters vol. 14, No. 20, pp. 1128-1130, Oct. 15, 1989.*

(Continued)

*Primary Examiner* — David Porta
*Assistant Examiner* — Edwin Gunberg
(74) *Attorney, Agent, or Firm* — Canon USA, Inc. IP Division

(57) ABSTRACT

The present invention provides a terahertz wave measuring apparatus and measurement method capable of improving the quantitativeness of obtained frequency spectrum information. In a measurement method in which a terahertz wave measuring apparatus is used, the terahertz wave measuring apparatus measures a time waveform of a terahertz wave relating to a calibration sample whose shape of a calibration spectrum is already known and obtains a measurement spectrum by transforming the time waveform. The calibration spectrum and the measurement spectrum are compared, and, on the basis of results of the comparison, time intervals of measurement data that form a time waveform are adjusted in order to calibrate the terahertz wave measuring apparatus.

15 Claims, 6 Drawing Sheets

(51) Int. Cl.
  *G01N 21/27* (2006.01)
  *G01N 21/3586* (2014.01)
  *G01J 3/02* (2006.01)

(56) References Cited

FOREIGN PATENT DOCUMENTS

| CN | 101210874 A | 7/2008 |
|---|---|---|
| CN | 101253403 A | 8/2008 |
| JP | 2002-139420 A | 5/2002 |
| JP | 2004-212110 A | 7/2004 |
| JP | 2007-101370 A | 4/2007 |
| JP | 2010-008139 A | 1/2010 |
| WO | 2009/050830 A1 | 4/2009 |

OTHER PUBLICATIONS

N.A. Thacker, "Error Propagation and the Fourier Transform" Dept. of Medical Biophysics, University of Manchester, Jan. 29, 1998, retrieved from the Internet Mar. 18, 2014.*

* cited by examiner

TERAHERTZ WAVE MEASURING APPARATUS AND MEASUREMENT METHOD

TECHNICAL FIELD

The present invention relates to a measuring apparatus and a measurement method for terahertz waves, and more particularly to a terahertz wave measuring apparatus (THz-time-domain spectroscopy (THz-TDS) apparatus) and a measurement method that measure terahertz waves in the time domain. More specifically, the present invention relates to a technology that improves the quantitativeness (the degree of re-liability of measured values) of the apparatus by calibrating a frequency spectrum obtained from a time waveform of a terahertz wave through a Fourier transform.

BACKGROUND ART

A terahertz wave is an electromagnetic wave that has a component anywhere in a frequency band of 0.03 THz to 30 THz. Characteristic absorptions (absorption of a particular frequency spectrum) resulting from biomolecules as well as from the structures and states of various substances often occur within such a frequency band. By utilizing such properties, inspection technologies through which substances are analyzed and identified in a nondestructive manner are being developed. In addition, the application of these technologies as safer imaging technologies that could replace x-rays and as high-speed communication technologies is desired. This kind of application often utilizes an absorption that is unique to a substance and that is observed as a frequency spectrum. In the case of a configuration of an apparatus that utilizes a frequency spectrum, the quantitativeness of measured frequency spectra is important. This requirement is not limited to the terahertz wave region. With respect to the infrared region, for example, there has been disclosed a technology in which an apparatus is calibrated by calculating a deviation between a theoretical waveform estimated from the optical parameters of a substance used for the calibration and a measurement waveform of the substance used for the calibration (PTL 1).

On the other hand, many THz-TDS apparatuses perform a sampling measurement by using ultrashort pulsed light (hereinafter may be referred to as excitation light) having a pulse width of femtosecond order in order to obtain a waveform having a pulse duration of sub-picosecond order. This sampling of a terahertz wave can be realized by adjusting a time difference between beams of excitation light that reach a generation unit that generates the terahertz wave and a detection unit that detects the terahertz wave, respectively. For example, the time difference is obtained by adjusting the amount of reflection of the excitation light with a stage (may be referred to as a delay optical unit herein) that has a reflection optical system and that is inserted into a propagation path of the excitation light. The accuracy with which a frequency spectrum is measured is influenced by the behavior of this stage. Therefore, there is disclosed a technology that improves the measurement accuracy by properly monitoring the position of the stage and obtaining the exact amount of reflection of the excitation light (PTL 2).

CITATION LIST

Patent Literature

PTL 1: Japanese Patent Laid-Open No. 2002-139420
PTL 2: Japanese Patent Laid-Open No. 2007-101370

SUMMARY OF INVENTION

Technical Problem

Frequency spectrum data in the terahertz wave region that has been introduced undesirably reflects the influence of the configurations of an apparatus and the measurement methods more than a little, and the spectral analyses therefor including simulations are not satisfactory. For this reason, if the technology disclosed in PTL 1 is applied to a measurement of a terahertz wave, it is difficult to obtain the information regarding a known substance by simply using the optical parameters of the terahertz wave region, which accordingly makes it difficult to define the theoretical waveform. Therefore, it is not easy to improve the quantitativeness of measured frequency spectra in the terahertz wave region.

The technology disclosed in PTL 2 is a proposal for improving the measurement accuracy by exactly reflecting the positional data of the stage that is included in the delay optical unit in the data of a time waveform. In this case, improvement of the measurement accuracies of individual apparatuses is expected. However, it is difficult to correct the variance in the quantitativeness of frequency spectra between apparatuses having different configurations, which have different positional deviations of the stage and different reading accuracies of the positional data.

In view of the technological situations described above, the following point is to be noted in the measurement of a terahertz wave, considering the differences in the configuration of the apparatuses such as the capability of the stage that is included in the delay optical unit described above and the difference in the measurement environments such as the atmosphere, the temperature, and the humidity that surround the measurement systems. That is, due to these differences, a deviation may be caused between the expected change in the optical-path length of the excitation light and the measured change in the optical-path length. As a result, even if the same sample is measured, a variation in the measurement results is caused between the measuring apparatuses, which raises concerns about the low quantitativeness of the obtained frequency spectrum information. Therefore, in the measurement of a terahertz wave, improvement of the quantitativeness of obtained frequency spectrum information is desired.

Solution to Problem

The present invention provides a measurement method using a terahertz wave measuring apparatus that measures a time waveform of a terahertz wave as measurement data by using time-domain spectroscopy, the measurement data being formed by including an intensity data stream and time intervals between elements of the intensity data stream, includes the following steps: a step of measuring a time waveform of a terahertz wave relating to a calibration sample whose calibration spectrum shape is already known by using the terahertz wave measuring apparatus; a step of obtaining a measurement spectrum by transforming the time waveform; a step of comparing the calibration spectrum and the measurement spectrum; and a step of calibrating the terahertz wave measuring apparatus by adjusting time intervals of measurement data that form the time waveform on the basis of results of the comparison.

In addition, the present invention provides a terahertz wave measuring apparatus that measures a time waveform of a terahertz wave by using time-domain spectroscopy includes the following elements: a generation unit configured to generate the terahertz wave; a detection unit configured to detect the terahertz wave that has been generated by the generation unit and that has propagated through a sample; a delay unit configured to adjust a delay time between a time when the terahertz wave is generated by the generation unit and a time when the terahertz wave is detected by the detection unit; a processing unit configured to refer to output of the detection unit and the delay unit and configured to obtain the time waveform of the terahertz wave as measurement data that is formed by including an intensity data stream and time intervals between elements of the intensity data stream; and a storage unit configured to store information relating to adjustment of the time intervals. The processing unit obtains the time waveform of the terahertz wave relating to a calibration sample whose calibration spectrum shape is already known, also obtains a measurement spectrum by transforming the time waveform, adjusts the time intervals of the measurement data that form the time waveform on the basis of results of comparison between the calibration spectrum and the measurement spectrum, and stores information relating to the adjustment in the storage unit.

Advantageous Effects of Invention

According to aspects of the present invention, an obtained measurement spectrum and a calibration spectrum are compared and, on the basis of the results of the comparison, the time intervals of measurement data that form a measured time waveform are adjusted. As a result, an apparatus that has been used and an apparatus that has measured the calibration spectrum (there may be a case in which the apparatuses are the same and the measurement environments are different) are calibrated to each other, which improves the quantitativeness of spectrum information to be output from the apparatus that has been used.

DESCRIPTION OF EMBODIMENTS

Figure 1:
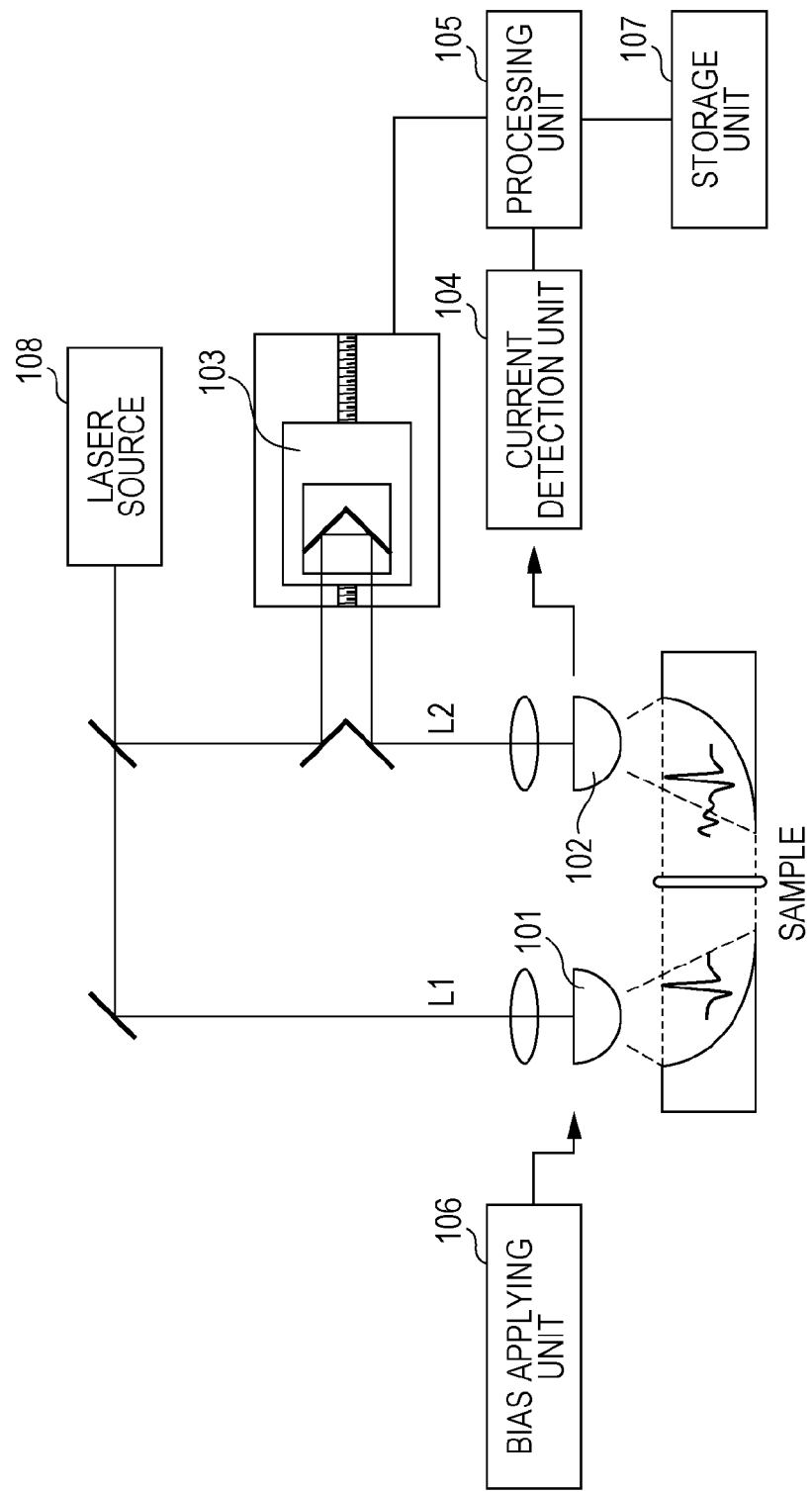
FIG. 1 is a schematic configuration diagram of an example of a measuring apparatus according to an embodiment of the present invention.

In the present invention, a measuring apparatus is calibrated by adjusting, on the basis of results of a comparison between a calibration spectrum and a measurement spectrum that have been obtained by using time-domain spectroscopy, the time intervals of measurement data that form a measured time waveform. On the basis of such an intention, a terahertz wave measuring apparatus and measurement method according to an embodiment of the present invention have the configuration described above as the basic configuration thereof. Here, the comparison is typically performed, for example, by comparing the position of a characteristic frequency that forms the shape of the calibration spectrum and the corresponding position of a characteristic frequency of a measurement spectrum. The position of a characteristic frequency may be the position of an absorption spectrum as in an example that will be described later, or may be the position of a frequency at which the transmittance or the like is highest or the position of the frequency of a point at which a line along a substantially plane portion of a spectrum and a line along an inclined portion of the spectrum intersect. The position of a characteristic frequency may be any position so long as the position is worth focusing upon and may be appropriately determined for each case. Content to be compared may be the significant figures or the variance (the difference between or the sum of the positions of characteristic frequencies) of the position of a frequency as in the example that will be described later, or may be a value that is calculated from differences in accordance with a certain expression, such as a variance obtained as the sum of the absolute values of differences or the sum of the squares of differences. Time intervals are typically adjusted by calculating, using a regression analysis method or the like, a coefficient of proportionality with which the time intervals are extended or shortened.

Embodiments capable of implementing the idea of the present invention will be described hereinafter with reference to the drawings. The present invention is applied to an apparatus that measures a terahertz wave in the time domain (THz-TDS apparatus). A signal in the time domain is formed of an intensity data stream and time intervals t between elements of the intensity data stream. The intensity data stream and the time intervals t that form a signal in the time domain may be collectively called "measurement data" herein. A measurement spectrum can be obtained by transforming a signal in the time domain into a signal in the frequency domain. In this embodiment, the time intervals t of measurement data are corrected in advance by using known calibration spectrum information such that measurement spectrum information matches the calibration spectrum information. To "match" herein means to satisfy matching conditions, an example f which will be described later. However, the matching conditions need to be defined from the perspective of improving the quantitativeness of spectrum information to be output from a measuring apparatus that is used. To calculate a coefficient for correcting the time intervals t by changing the value of the coefficient until the matching conditions are satisfied may be referred to as "calibration" herein. When a coefficient of proportionality for correcting the time intervals t is denoted by a, a sample in this embodiment is measured with the time intervals being represented by an expression a X t. In this case, calibration can also be performed by appropriately dividing the time domain into a plurality of time ranges and obtaining coefficients a1, a2, and so on for the time ranges. However, the division of the time domain into the time ranges also needs to be performed from the perspective of improving the quantitativeness of spectrum information to be output from a measuring apparatus.

FIG. 1 is a general configuration diagram of an example of a terahertz wave measuring apparatus according to an embodiment of the present invention. The apparatus illustrated in FIG. 1 adopts the basic configuration of a THz-TDS apparatus and measures the time waveform of a terahertz wave in the time domain. In FIG. 1, units for which the configuration of a measuring apparatus of the related art is adopted include a generation unit 101, a detection unit 102, a delay optical unit 103, a current detection unit 104, a processing unit 105, a bias applying unit 106, and a laser source 108. The processing unit 105 serves as a unit that calculates the coefficient a, which is a characteristic of the present invention, for correcting the time intervals t of measurement data, and the result is stored in a storage unit 107. The storage unit 107 may perform the function of calculating the coefficient a for correcting the time intervals t of measurement data, instead. During a measurement of a sample after calibration, the measuring apparatus refers to the coefficient a for correction stored in the storage unit 107 to adjust the time intervals t of measurement data of the sample, and then performs the measurement.

First, the units for which the configuration of the measuring apparatus of the related art is adopted will be described.

The generation unit 101 is a unit that generates a terahertz wave. The generation principle adopted by the generation unit 101 may be a method utilizing a momentary current or a method utilizing the interband transition of carriers. The method utilizing a momentary current includes a method that generates a terahertz wave by irradiating the surface of a semiconductor or an organic crystal with excitation light. This method may be one in which an element (photoconductive element) that has been obtained by forming an antenna pattern on a thin semiconductor film using a metal electrode is irradiated with excitation light in a state in which an electric field is applied to the element. In addition, a PIN diode can be applied. As the method utilizing the interband transition of carriers in a gain structure, a method using a semiconductor quantum well structure can be applied.

The detection unit 102 is a unit that detects the field intensity of a terahertz wave. The detection principle adopted by the detection unit 102 may be a method in which a current corresponding to the field intensity of a terahertz wave is detected on the basis of a change in the photoconductivity upon the radiation of excitation light. For such a method for detecting a current, the above-mentioned photoconductive element can be applied. In addition, there are also a method for detecting an electric field using an electro-optical effect and a method for detecting a magnetic field using a magneto-optical effect. As the method for detecting an electric field using an electro-optical effect, a method using a polarization splitter and an electro-optical crystal can be applied. As the method for detecting a magnetic field using a magneto-optical effect, a method using a polarization splitter and a magneto-optical crystal can be applied. An example in which photoconductive elements are used as the generation unit 101 and the detection unit 102 will be described herein.

The laser source 108 is a unit that outputs an ultrashort pulse laser. The generation unit 101 and the detection unit 102 that have been described above operate when carriers are excited into the thin semiconductor film by radiation of the ultrashort pulse laser. For this reason, the ultrashort pulse laser is called "excitation light" herein. As illustrated in FIG. 1, the excitation light diverges into two beams that propagate along two optical paths L1 and L2. Here, the generation unit 101 is irradiated with a beam of excitation light that propagates along the optical path L1. The detection unit 102 is irradiated with a beam of excitation light that propagates along the optical path L2 through the delay optical unit 103, which will be described later.

The time waveform of a terahertz wave is in many cases a pulse waveform of shorter than one picosecond and is therefore hard to obtain in real time. For this reason, sampling measurement of the time waveform of a terahertz wave is performed using the above-mentioned excitation light. The delay optical unit 103, which is a delay unit that adjusts the delay time between the generation of a terahertz wave performed by the generation unit 101 and the detection of the terahertz wave performed by the detection unit 102, is a unit that adjusts the position at which the sampling is performed in data that forms the time waveform of a terahertz wave. More specifically, the delay optical unit 103 delays the arrival time of the excitation light with which the detection unit 102 is irradiated in relation to the arrival time of the excitation light with which the generation unit 101 is irradiated. A method for adjusting the time difference between the two beams of excitation light that reach the generation unit 101 and the detection unit 102, respectively, may be a method in which the length of an optical-path along which a beam of the excitation light propagates is directly adjusted or a method in which the effective optical-path length is adjusted. As the method in which the optical-path length is directly adjusted, there is a method using a reflection optical system that reflects the excitation light and a movable unit that moves the reflection optical system in a reflecting direction. As the method in which the effective optical-path length is adjusted, there is a method in which the time constant (index of refraction) of an optical path along which a beam of the excitation light propagates is changed. FIG. 1 illustrates an example in which a single-stage reflection optical system and a translation stage as a movable unit are used. By adjusting the position of the reflection optical system with the movable unit, the length of the optical path L2 extending from the laser source 108 to the detection unit 102 is changed. By utilizing the change in the optical-path length, the time difference between the two beams of excitation light that reach the generation unit 101 and the detection unit 102, respectively, is calculated from the difference between the lengths of the optical paths L2 and L1 and adjusted. The faster the driving speed of the movable unit, the shorter the time taken to obtain the time waveform of a terahertz wave.

The bias applying unit 106 is a unit that supplies a bias for driving the generation unit 101. When a photoconductive element is used as the generation unit 101, voltage is applied to a metal electrode that includes an antenna pattern. In particular, when the current detection unit 104, which will be described later, includes a lock-in detection system, the voltage supplied by the bias applying unit 106 is modulated at a frequency equal to that of a reference signal of the lock-in detection system. When lock-in detection is performed, not only the bias supplied by the bias applying unit 106 but also a light chopper may be adopted in a modulation method. In that case, the bias applying unit 106 applies a direct current bias to the photoconductive element.

The current detection unit 104 is a unit that converts a current signal into a voltage signal having a measurable level. When a photoconductive element is used as the detection unit 102, the current detection unit 104 converts a current signal output from the detection unit 102 into a voltage signal. The conversion ratio at which a current signal is converted into a voltage signal is called the "current-voltage conversion ratio". The current-voltage conversion ratio is selected from a certain range in relation to a current signal input to the current detection unit 104, so that the output of the current detection unit 104 does not exceed the rating of a circuit and is not saturated. In order to improve the signal-to-noise ratio of the measuring apparatus, the current-voltage conversion ratio is preferably made larger. As described above, when a signal output from the detection unit 102 is small, the current detection unit 104 may include the lock-in detection system. More specifically, the lock-in detection system is arranged at a stage subsequent to a circuit that performs the current-voltage conversion. When the lock-in detection system is included, the output of the circuit that performs the current-voltage conversion is adjusted in a certain range, so that the output does not exceed the input rating of the lock-in detection system.

The processing unit 105 is a unit that constructs the time waveform of a terahertz wave and that creates measurement data. The time waveform is constructed by referring to the amount of change in the optical-path length caused by the delay optical unit 103 and the output of the current detection unit 104. More specifically, the time waveform is constructed by plotting the output of the current detection unit 104 for each optical-path length that is sequentially changed by a certain amount. The amount of change in the optical-path length corresponds to the time intervals t of measurement data. The plotted data is then stored as the intensity data stream of the measurement data. In order to improve the signal-to-noise ratio of the measuring apparatus, there is a method for constructing the time waveform by stopping the movement of the translation stage that is included in the delay optical unit 103 (or driving the translation stage at a speed slow enough to be regarded as being stationary) at each measurement point and averaging the output of the current detection unit 104. This method is also called a "step-scan method". In addition, there is a method in which the translation stage that is included in the delay optical unit 103 is driven at high speed, in which the time waveform is obtained more than once, and in which each element of the intensity data stream of measurement data is averaged by the processing unit 105. This method is also called a "rapid-scan method".

In a case of outputting spectrum data in the frequency domain is output, the processing unit 105 refers to measurement data and performs a Fourier transform on the time waveform of a terahertz wave in order to obtain the spectrum data. When the THz-TDS apparatus is used as an analysis apparatus, a change in the time waveform when a sample is irradiated with a terahertz wave is calculated. In addition, the processing unit 105 can obtain an image by monitoring the relative position between the sample and the terahertz wave with which the sample is irradiated. With the configuration described above, the THz-TDS apparatus monitors the change in the optical-path length of the excitation light caused by the delay optical unit 103 and the corresponding change in the output of the current detection unit 104 in order to construct the time waveform of a terahertz wave with which the detection unit 102 is irradiated.

Figure 2:
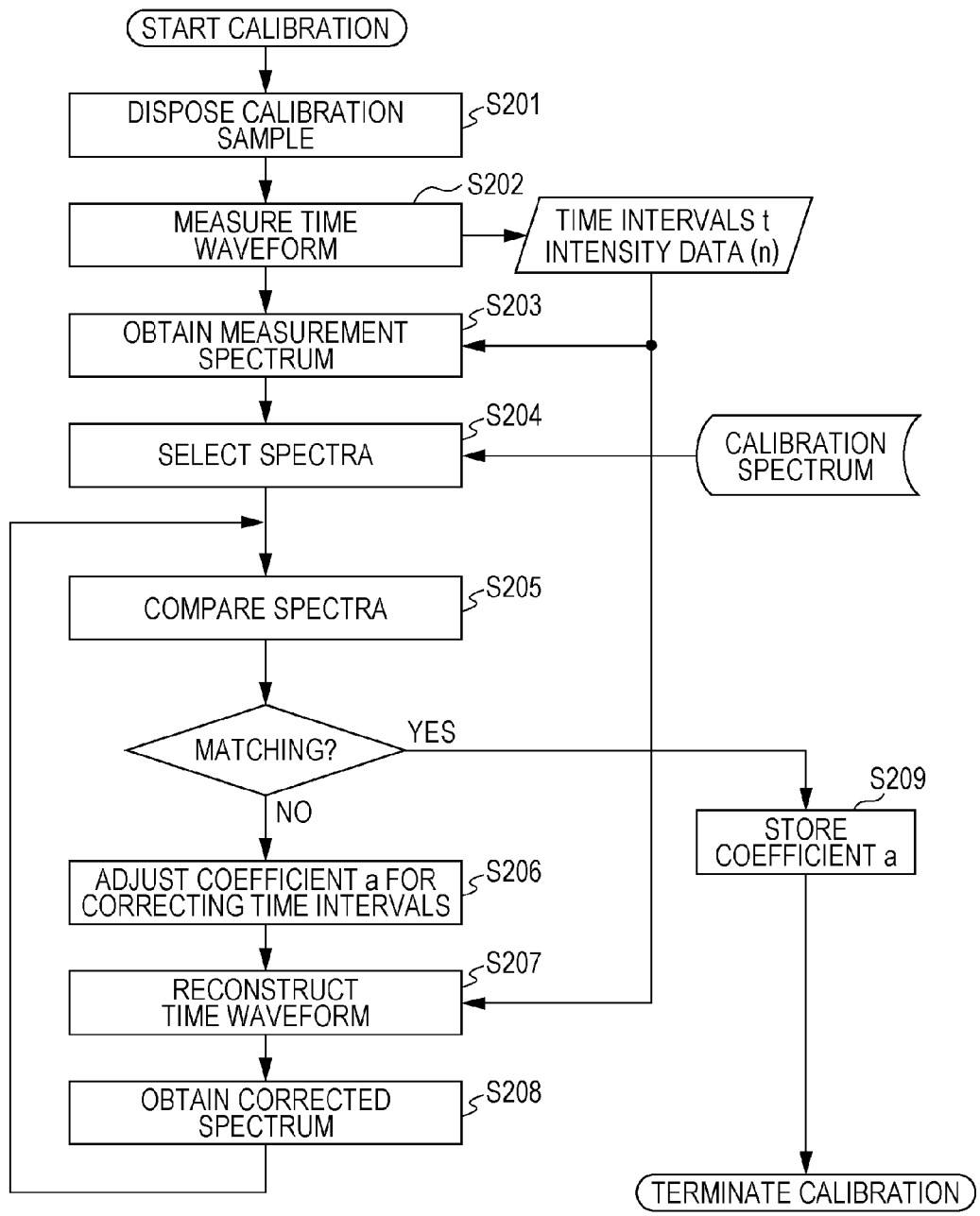
FIG. 2 is an operational flowchart of an example of the measuring apparatus and a measurement method according to the embodiment of the present invention.
Figure 3A:
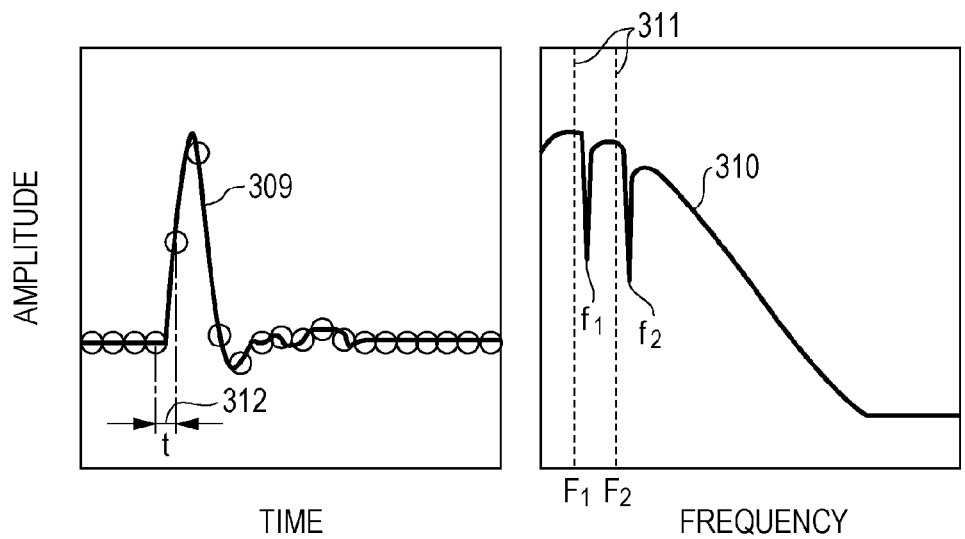
FIG. 3A is a diagram illustrating an example of the operation of the measuring apparatus and the measurement method according to the embodiment of the present invention.
Figure 3B:
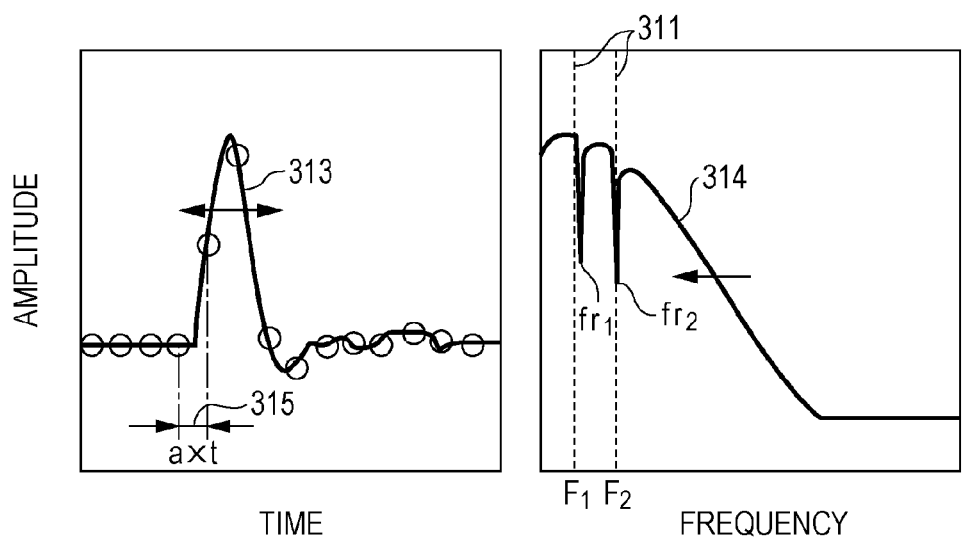
FIG. 3B is a diagram illustrating an example of the operation of the measuring apparatus and the measurement method according to the embodiment of the present invention.

In addition to the configuration described above, the terahertz wave measuring apparatus according to this embodiment has the storage unit 107 that calculates the co-efficient a for correcting the time intervals t of measurement data and that stores the coefficient a. The coefficient a is calculated by comparing measurement results of a calibration sample that are obtained by the apparatus and information regarding a calibration spectrum that is attached in advance to the calibration sample. The operation performed until the coefficient a for correcting the time intervals t is obtained will be described with reference to FIGS. 2, 3A and 3B. FIG. 2 is a flowchart of the operation performed until the coefficient a for correcting the time intervals t is obtained. FIGS. 3A and 3B illustrate the operation of the apparatus during this time. It is to be noted that the steps for obtaining the coefficient a for correcting the time intervals t are not limited to those in the illustrated example. The steps may be switched, increased, or deleted in accordance with the configuration of the apparatus, so long as an object that the coefficient a for correcting the time intervals t is obtained is achieved.

When calibration of the apparatus is started, a calibration sample is disposed in a path along which a terahertz wave propagates (S201 of FIG. 2). As illustrated in FIGS. 3A and 3B, a calibration spectrum 311 is attached to the calibration sample in advance, and therefore characteristic positions ($F_1$ and $F_2$) that form the calibration spectrum 311 can be identified. As a calibration sample to be used, a sample such as glucose or maltose in which a characteristic spectrum such as an absorption spectrum exists in a terahertz wave region is appropriate. An example of a substance in which a spectrum extends over a wide range and that has a wide application range as a calibration sample is water vapor. In addition, a structure that structurally generates a spectrum, such as a filter or a photonic crystal, may be adopted as a calibration sample.

When the calibration sample is disposed at a certain position, the measuring apparatus performs a measurement of the time waveform of a terahertz wave (S202 of FIG. 2). The time waveform of a terahertz wave is, as can be observed in a measurement waveform 309 of FIG. 3A, obtained as an intensity data stream formed of a number of pieces of data of n corresponding to constant time intervals t 312. In this embodiment, this information is stored in the processing unit 105 as measurement data. When the time waveform of the terahertz wave has been obtained, the processing unit 105 refers to the stored measurement data to obtain a measurement spectrum 310 of FIG. 3A in the frequency domain (S203 of FIG. 2). The time intervals t 312 in the measurement data determine the maximum frequency of the measurement spectrum 310. The number of elements n of the intensity data stream determines the frequency resolution of the measurement spectrum 310. As illustrated in FIG. 3A, characteristic positions ($f_1$ and $f_2$) that form the measurement spectrum 310 exist in the measurement spectrum 310.

The processing unit 105 obtains the measurement spectrum 310 as well as calling up the calibration spectrum 311 of the calibration sample stored in the storage unit 107. The calibration spectrum 311 and the measurement spectrum 310 are both shown in FIG. 3A, which illustrates the state before the calibration. The processing unit 105 selects spectra to be calibrated in accordance with the shapes of the calibration spectrum 311 and the measurement spectrum 310 (S204 of FIG. 2). With respect to the selection of spectra, all characteristic spectra may be selected or one or more spectra to be focused upon may be selected from among a plurality of spectra. It is desirable to perform the calibration ideally for all the characteristic spectra; however, there may be positions that are hard to calibrate depending on the difference in the capacity of the apparatus (for example, the frequency resolution or the frequency measurement range). Therefore, by flexibly selecting the spectra to be used for the calibration in accordance with the capacity of the apparatus to be used, the versatility of the apparatus can be improved. The positions $F_1$ and $F_2$ are selected herein as the positions of the spectra to be used for the calibration.

As illustrated in FIG. 3A, a position of the measurement spectrum 310 corresponding to the position $F_1$ of the calibration spectrum 311 is the position $f_1$. Similarly, a position of the measurement spectrum 310 corresponding to the position $F_2$ of the calibration spectrum 311 is the position $f_2$. After selecting the spectra to be used for the calibration, the processing unit 105 performs a spectrum comparison in which the positions of the two along the frequency axis are compared (S205 of FIG. 2). By this comparison, it is determined whether or not the two spectra satisfy the matching conditions. The matching conditions herein refer to conditions under which the spectra perfectly match each other within significant figures, which are determined in terms of the positions along the frequency axis. However, the matching conditions are not limited to the perfect matching as in this case. The matching conditions may refer to conditions under which the measurement spectrum 310 whose variance relative to the calibration spectrum 311 has been calculated is located within an expected region. For example, if five characteristic positions of spectra are selected, the matching conditions refer to conditions under which the variances of all the five positions are within a certain range of values. In addition, conditions under which the variances of the positions of spectra of a predetermined ratio are smallest may be regarded as the matching conditions. For example, if the variances of the positions of spectra of 80% or more need to be within a certain range of values, the matching conditions refers to conditions under which the variances of four positions are smallest or four positions perfectly match the corresponding ones (the variances are zero). Thus, the matching conditions are determined by a measurer. As illustrated in FIG. 3A, the positions $f_1$ and $f_2$ of the measurement spectrum 310 deviate on the higher frequency side in relation to the calibration spectrum 311, which will be regarded as not satisfying the matching conditions in the following description.

If the matching conditions are not satisfied, the processing unit 105 changes the time intervals t 312 of the measurement data (S206 of FIG. 2). In this process, the time intervals before the change are called the "first time intervals" and the time intervals after the change are called the "second time intervals" for convenience of description. The coefficient a for correcting the time intervals t 312 corresponds to the value obtained by dividing the changed time intervals by the time intervals t 312 of the measurement waveform 309. Therefore, both the first time intervals and the second time intervals can be represented by an expression a X t, but the value of the coefficient a is different between the first time intervals and the second time intervals. In addition, in the case of the time intervals t 312 of the measurement waveform 309, the coefficient a is 1.

After the first time intervals of the measurement data is changed to the second time intervals, a corrected waveform 313 of FIG. 3B is reconstructed (S207 of FIG. 2). As illustrated in FIG. 3B, time intervals 315 at this time are represented by an expression a X t. The processing unit 105 then obtains a corrected spectrum 314 from the corrected waveform 313 (S208 of FIG. 2). As illustrated in FIGS. 3A and 3B, if the corrected waveform 313 extends along the time axis wider than the measurement waveform 309, the measurement spectrum 310 is compressed on the lower range side to be the corrected spectrum 314. In this condition, the selected positions of the calibration spectrum 311 ($F_1$ and $F_2$) and the corrected spectrum 314 ($fr_1$ and $fr_2$) are compared. The steps S205 to S208 are repeatedly performed until the matching conditions of the spectra are satisfied. If it is determined that the matching conditions are satisfied, the coefficient a for correcting the time intervals t 312 at the time is stored in the storage unit 107 (S209 of FIG. 2).

As described above, in this embodiment, the obtained measurement spectrum 310 and the calibration spectrum 311 are compared in order to calculate the coefficient a with which the time intervals t 312 that form the measurement data of the measurement waveform 309 are corrected, so that the selected positions of the two spectra match each other. As a result, since the measurement of a terahertz wave is performed after the apparatus that has been used and the apparatus that has measured the calibration spectrum 311 are calibrated to each other, the quantitativeness of spectrum information to be output from the apparatus that has been used is improved.

When an unknown sample is measured, the measurement is performed by referring to the coefficient a for correction stored in the storage unit 107 and correcting the time intervals t to the time intervals a X t. This correction corresponds to adjusting the time axis originally included in the measuring apparatus in accordance with the coefficient a for correcting the time intervals t. For example, if the time waveform of a terahertz wave expands along the time axis, a frequency spectrum that is obtained by transforming the time waveform contracts to the lower range side. This is because the period of each frequency element that forms the time waveform expands. In contrast, if the time waveform of a terahertz wave contracts along the time axis, a frequency spectrum that is obtained by transforming the time waveform expands to the higher range side. By matching the obtained spectrum information to the calibration spectrum information through this adjustment of the time axis, the apparatus that has measured the calibration sample and the apparatus according to an embodiment of the present invention are calibrated to each other. As has been seen, since a terahertz wave is measured in a state in which the apparatus that is used and the apparatus that has measured the calibration spectrum have been calibrated to each other, an apparatus whose quantitativeness of spectrum information is improved can be constantly provided.

During the measurement of a sample, the measuring apparatus refers to the co-efficient a for correcting the time intervals stored in the storage unit 107 in order for the processing unit 105 to correct and output the time intervals of the measurement data, which is the results of the measurement. That is, the time axis is adjusted by performing post-processing on the time intervals of the obtained measurement data in accordance with the coefficient a. By using this method, the configuration according to an embodiment of the present invention can be easily introduced without largely changing the configuration of a measuring apparatus that has been constructed. In addition, not as the post-processing but during the measurement, the distance over which the delay optical unit 103 needs to travel between the elements of measurement data may be directly changed in accordance with the coefficient a for correcting the time intervals stored in the storage unit 107. That is, the adjustment of the time intervals of measurement data can be performed by adjusting the amount of change in the difference of the optical-path lengths that is caused by the delay optical unit 103 and that corresponds to the time intervals of the elements of an intensity data stream. In this case, the post-processing step for the calibration can be omitted, which simplifies the apparatus. In other words, in the former case, calibration is performed as processing in the processing unit 105 while calibration is performed by controlling the delay optical unit 103, that is, by controlling hardware, in the latter case.

It is to be noted that although the difference between apparatuses is considered as a primary target and the coefficient of the apparatus is calculated in the calibration method described above, the target of calibration is not limited to this. For example, even if the same apparatus is used, the difference in measurement environments may be considered as a primary target and a coefficient of an environment may be calculated. In addition, during the measurement of a sample, the time intervals t may be adjusted by multiplying the coefficient of the apparatus and that of the environment in accordance with the apparatus to be used and the measurement environment during the measurement.

In the calibration according to an embodiment of the present invention, information regarding a sample that has been used for the calibration is important. More specifically, the detailed information regarding the calibration sample such as the fabrication conditions and the seller as well as the environment information such as the atmosphere in which the calibration spectrum 311 has been measured and the system configuration are important. Therefore, when the data of the measuring apparatus is output to an external device, information relating to the calibration spectrum 311 and the calibration sample that have been used by the terahertz wave measuring apparatus for the measurement are preferably attached. That is, the measuring apparatus preferably includes an output unit that outputs the measurement data (the corrected spectrum 314) as well as the information used for the calibration of the apparatus. By adopting such usage, a more exact calibration is possible, which makes it easy for a recipient of the information to verify the measurement data in a state in which the variation in data between apparatuses is reduced. As a result, the information can be more widely shared and the reliability of the data can be improved.

More specific examples will be described hereinafter.

EXAMPLE 1

Example 1 of the calibration of the apparatus will be described. More specifically, an example of calibration in which the coefficient of the measuring apparatus was calculated and the variation in data caused by the difference between the apparatuses was reduced will be described. Measurement data of a sample that had been measured by another apparatus was used for a calibration spectrum. The sample that had been used at that time was glucose containing polyethylene as a binder (content of 10%).

As a calibration sample, glucose containing polyethylene as a binder (content of 5%) was used. The calibration sample used to obtain a measurement spectrum was prepared by a worker who performed the calibration in order to perform a measurement using an apparatus with which the calibration was performed.

Figure 4A:
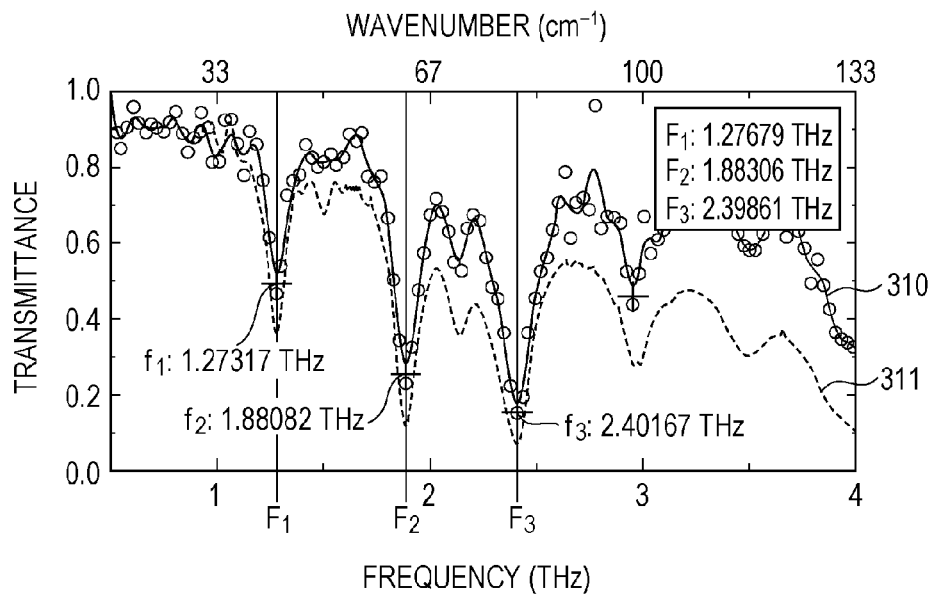
FIG. 4A is a diagram illustrating the calibration operation of Example 1 in the embodiment of the present invention.
Figure 4B:
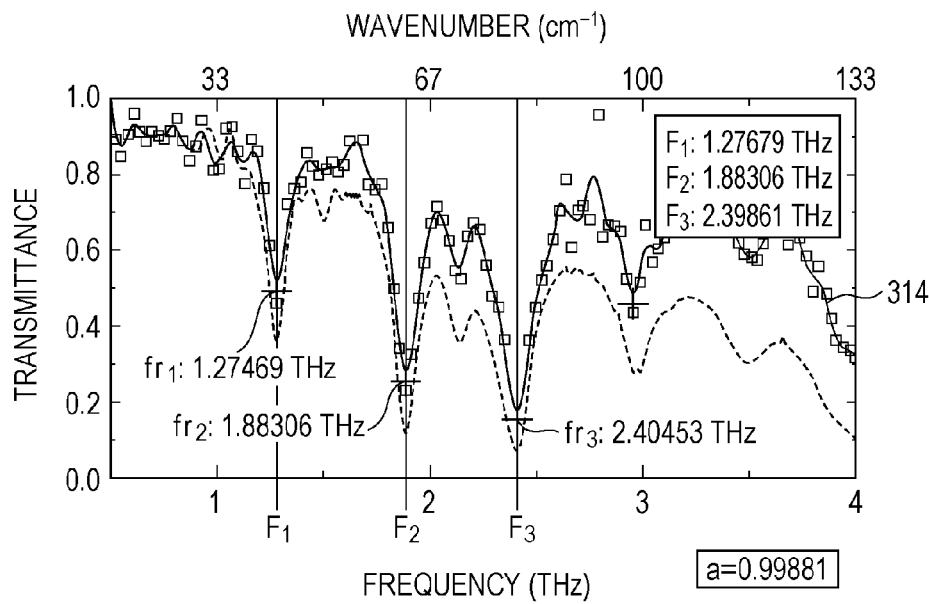
FIG. 4B is a diagram illustrating the calibration operation of Example 1 in the embodiment of the present invention.

FIGS. 4A and 4B illustrate a frequency spectrum before the calibration and a frequency spectrum after the calibration. The calibration spectrum 311 is represented by a broken line. As characteristic positions that form the shape of the calibration spectrum 311, a position $F_1$ of 1.27679 THz, a position $F_2$ of 1.88306 THz, and a position $F_3$ of 2.39861 THz were selected. The measurement spectrum 310 was calculated by performing five-point smoothing using the Savitzky-Golay method on frequency spectrum data that was obtained by transforming measurement data. Although the transmittance that was obtained by using the binder as a reference is plotted along the vertical axis of FIG. 4A and 4B, an intensity spectrum of the calibration sample may be used instead. Positions of frequencies of the measurement spectrum 310 corresponding to the positions $F_1$ to $F_3$ were position $f_1$ of 1.27317 THz, a position $f_2$ of 1.88082 THz, and a position $f_3$ of 2.40167 THz, respectively.

The position $F_2$ was calibrated in this example. The matching conditions at that time were determined to be conditions under which the positions perfectly match each other within significant figures of frequencies of five decimal places. In the calibration performed under these matching conditions, the position $F_2$ in the frequencies of the calibration spectrum 311 and a position $fr_2$ in the frequencies of the corrected frequency 314 matched each other when the coefficient a for correcting the time intervals was 0.99881 as illustrated in FIG. 4B. Thus, in this example, the quantitativeness of spectrum data at least around the position $F_2$ was improved even if the measuring apparatuses were different.

EXAMPLE 2

Example 2 of the calibration of the apparatus will be described. More specifically, an example of calibration in which the coefficient of the environment was calculated and in which the variation in data caused by the difference between the measurement environments was reduced will be described. With respect to the measurement environments, spectrum data was calibrated in a situation in which the atmosphere around the measuring apparatus was replaced by nitrogen and in a situation in which the atmosphere around the measuring apparatus was vacuum. Measurement data of a sample that had been measured in the situation in which the atmosphere of the measuring apparatus had been replaced by nitrogen was used for a calibration spectrum. The sample that had been used at that time was maltose (100%).

As a calibration sample, maltose containing polyethylene as a binder (content of 5%) was used. The calibration sample had been separately prepared before the calibration was performed. A measurement spectrum was obtained by measuring the calibration sample in the situation in which the atmosphere of the measuring apparatus was vacuum.

Figure 5A:
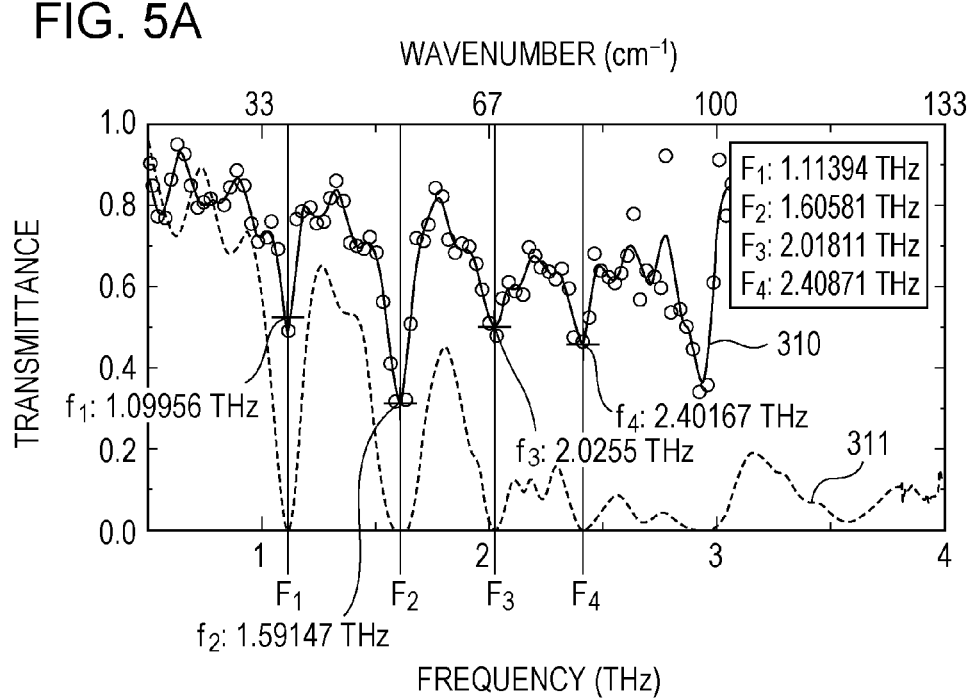
FIG. 5A is a diagram illustrating the calibration operation of Example 2 in the embodiment of the present invention.
Figure 5B:
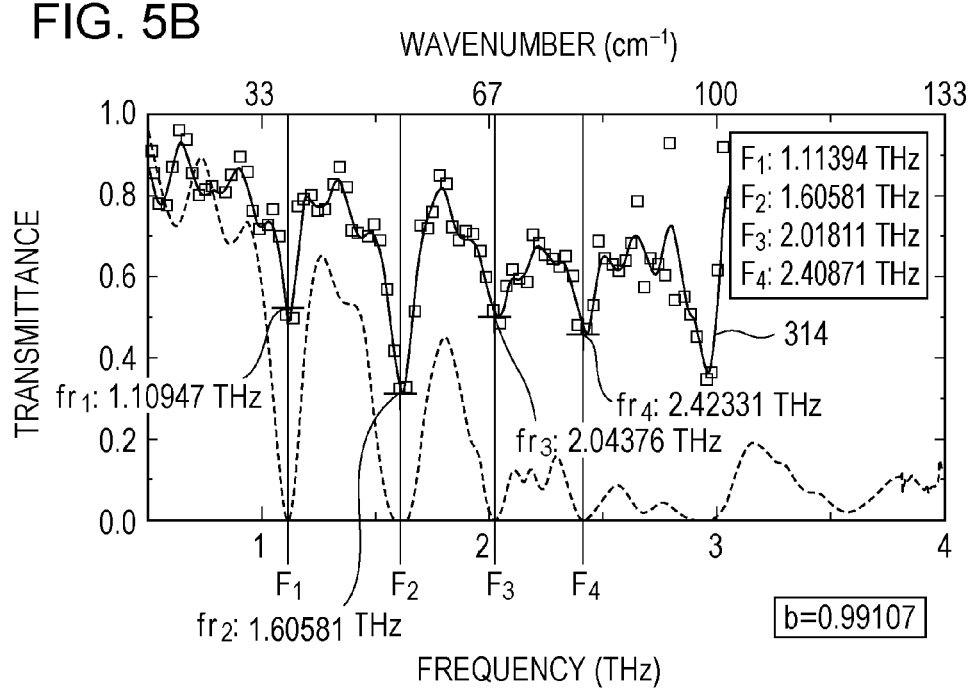
FIG. 5B is a diagram illustrating the calibration operation of Example 2 in the embodiment of the present invention.

FIGS. 5A and 5B illustrate a frequency spectrum before the calibration and a frequency spectrum after the calibration. The calibration spectrum 311 is represented by a broken line. As characteristic positions that form the shape of the calibration spectrum 311, a position $F_1$ of 1.11394 THz, a position $F_2$ of 1.60581 THz, a position $F_3$ of 2.01811 THz, and a position $F_4$ of 2.40871 THz were selected. The measurement spectrum 310 was calculated by performing five-point smoothing using the Savitzky-Golay method on frequency spectrum data that was obtained by transforming measurement data. Although the transmittance that was obtained by using the binder as a reference is plotted along the vertical axis of FIGS. 5A and 5B, an intensity spectrum of the calibration sample may be used instead. Positions of frequencies of the measurement spectrum 310 corresponding to the positions $F_1$ to $F_4$ were position $f_1$ of 1.09956 THz, a position $f_2$ of 1.59147 THz, a position $f_3$ of 2.02250 THz, and a position $f_4$ of 2.40167 THz, respectively.

The position $F_2$ was calibrated in this example. The matching conditions at that time were determined to be conditions under which the positions perfectly match each other within the significant figures of frequencies of five decimal places. In the calibration performed under these matching conditions, the position $F_2$ in the frequencies of the calibration spectrum 311 and a position $fr_2$ in the frequencies of the corrected frequency 314 matched each other when the coefficient a for correcting the time intervals was 0.99107 as illustrated in FIG. 5B. Thus, in this example, the quantitativeness of spectrum data at least around the position $F_2$ was improved even if the measurement environments were different.

EXAMPLE 3

Example 3 is a modification of Example 1. More specifically, the matching conditions were different. The matching conditions at that time were conditions under which the variance (the sum of differences) of the calibration spectrum and the corrected spectrum is smallest at a plurality of positions of frequencies of a characteristic spectrum.

Figure 6:
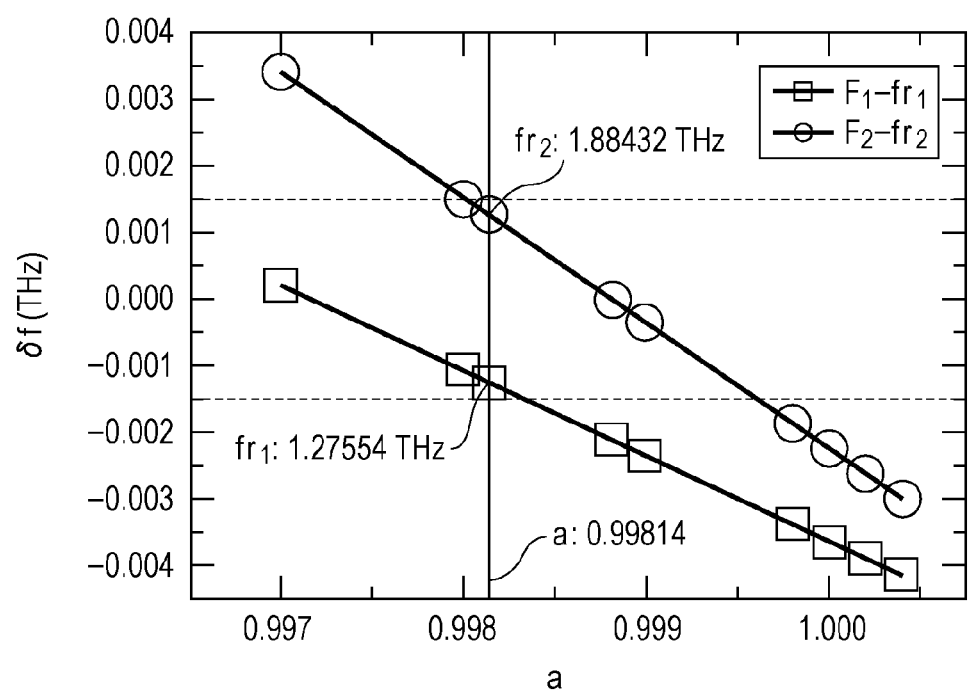
FIG. 6 is a diagram illustrating the calibration operation of Example 3 in the an embodiment of the present invention.

FIG. 6 illustrates the results of the calibration. FIG. 6 illustrates the differences df of the spectra, which are represented by an expression F-fr, at the position $F_1$ of 1.27679 THz and the position $F_2$ of 1.88306 THz of FIG. 4B caused by the difference in the coefficient a for correcting the time intervals. According to FIG. 6, when the coefficient a for correcting the time intervals was 0.99814, the position $fr_1$ in the frequencies was 1.27554 THz and the position $fr_2$ in the frequencies was 1.88432 THz in the corrected spectrum 314, which were nearest to the calibration spectrum (the sum of the differences df approximates zero). Thus, by performing calibration for a plurality of positions, the quantitativeness of a region extending from the position $F_1$ to the position $F_2$ was improved.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-056197, filed Mar. 12, 2010, which is hereby incorporated by reference herein in its entirety.

The invention claimed is:

1. A calibration method for calibrating a THz-TDS apparatus that obtains a time waveform of a terahertz wave by detecting the terahertz wave at time intervals, the calibration method comprising the steps of:
obtaining a time waveform of a terahertz wave propagating through a calibration sample, by using the THz-TDS apparatus;
obtaining a measurement spectrum in a frequency domain by transforming the time waveform of the terahertz wave propagating through the calibration sample;
comparing a calibration spectrum of the calibration sample and the measurement spectrum; and
changing the time intervals for detection by the THz-TDS apparatus or a time axis of the time waveform obtained by the THz-TDS apparatus on the basis of results of the comparison.

2. The calibration method according to claim 1,
wherein, in the step of comparing, a position of a characteristic frequency that forms a shape of the calibration spectrum and a position of a characteristic frequency of the measurement spectrum that corresponds to the aforementioned position are compared, and
wherein, in the step of changing, a coefficient of proportionality, that changes first time intervals for detection by the THz-TDS apparatus to second time intervals or a coefficient of proportionality that changes a first time axis of the time waveform obtained by the THz-TDS apparatus to a second time axis is obtained such that results of the comparison between the position of the characteristic frequency of the calibration spectrum and the position of the characteristic frequency of the measurement spectrum satisfy certain matching conditions.

3. The calibration method according to claim 2,
wherein, in the step of comparing, a position to be focused upon is selected from among a plurality of positions of characteristic frequencies that form the shape of the calibration spectrum and compared with a corresponding position in the measurement spectrum.

4. The calibration method according to claim 1, wherein the comparison is performed by obtaining a difference between a position of a characteristic frequency that forms the shape of the calibration spectrum and a position of a characteristic frequency of the measurement spectrum that corresponds to the aforementioned position or by obtaining a value that is calculated from the difference in accordance with a certain expression, and
wherein the step of changing is performed by using a regression analysis method in which the results of the comparison are used.

5. A THz-TDS apparatus comprising:
a generation unit configured to generate a terahertz wave;
a detection unit configured to detect a terahertz wave propagating through a sample at time intervals; and
a processing unit configured to use results of the detection by the detection unit to obtain a time waveform of the terahertz wave,
wherein the processing unit obtains a time waveform of a terahertz wave propagating through a calibration sample, obtains a measurement spectrum in a frequency domain by transforming the time waveform of the terahertz wave propagating through the calibration sample, compares a calibration spectrum of the calibration sample and the measurement spectrum, and changes the time intervals for detection by the detection unit or a time axis of the time waveform obtained by the processing unit on the basis of results of the comparison.

6. The THz-TDS apparatus according to claim 5, comprising a delay unit configured to adjust a delay time between a time when the terahertz wave is generated by the generation unit and a time when the terahertz wave is detected by the detection unit,
wherein, in a case where an unknown sample is measured, the processing unit changes the time intervals for detection by the detection unit by changing the delay time adjusted by the delay unit on the basis of the results of the comparison, and measures a time waveform of a terahertz wave propagating through the unknown sample in a state where the time intervals for detection by the detection unit has been changed.

7. The THz-TDS apparatus according to claim 5, wherein the time axis is changed by processing performed by the processing unit.

8. The THz-TDS apparatus according to claim 5, wherein the delay unit is a delay optical unit configured to adjust the delay time by changing a difference between an optical path length of excitation light that reaches the generation unit and an optical path length of excitation light that reaches, and
wherein the time intervals for detection by the detection unit are changed by adjusting the amount of change, which is caused by the delay optical unit, in the difference.

9. The THz-TDS apparatus according to claim 5, further comprising:
an output unit configured to output the results of the detection at the time intervals by the detection unit, together with information relating to the calibration spectrum.

10. The THz-TDS apparatus according to claim 5, wherein the processing unit expands or contracts the time intervals for detection by the detection unit or the time axis of the time waveform obtained by the processing unit so as to bring the measurement spectrum close to the calibration spectrum.

11. The THz-TDS apparatus according to claim 5, wherein the processing unit compares the calibration spectrum and the measurement spectrum, and then the processing unit expands the time intervals for detection by the detection unit or the time axis of the time waveform obtained by the processing unit if the measurement spectrum extends on a higher range side than the calibration spectrum, and contracts the time intervals for detection by the detection unit or the time axis of the time waveform obtained by the processing unit if the measurement spectrum compresses on a lower range side than the calibration spectrum.

12. The THz-TDS apparatus according to claim 5, further comprising a storage unit configured to store information relating to change of the time intervals for detection by the detection unit or change of the time axis of the time waveform obtained by the processing unit.

13. The THz-TDS apparatus according to claim 12, wherein the storage unit stores information relating to the calibration sample.

14. A calibration method for calibrating a THz-TDS apparatus that obtains a time waveform of a terahertz wave by detecting the terahertz wave at time intervals, the calibration method comprising the steps of:
    measuring a time waveform of a terahertz wave propagating through a calibration sample by using the THz-TDS apparatus; and
    changing the time intervals for detection by the THz-TDS apparatus or a time axis of the time waveform obtained by the THz-TDS apparatus on the basis of information relating to the calibration sample and information relating to the time waveform of the terahertz wave propagating through the calibration sample.

15. A THz-TDS apparatus comprising:
a generation unit configured to generate a terahertz wave;
a detection unit configured to detect a terahertz wave propagating through a sample at time intervals; and
a processing unit configured to use results of the detection by the detection unit to obtain a time waveform of the terahertz wave,
wherein the processing unit obtains a time waveform of a terahertz wave propagating through a calibration sample, and changes the time intervals for detection by the detection unit or a time axis of the time waveform obtained by the processing unit on the basis of information relating to the calibration sample and information relating to the time waveform of the terahertz wave propagating through the calibration sample.

* * * * *